(12) United States Patent
Do

(10) Patent No.: US 11,464,959 B2
(45) Date of Patent: Oct. 11, 2022

(54) METHOD AND APPARATUS FOR ENHANCING THE MATURATION RATE OF AN ARTERIOVENOUS FISTULA

(71) Applicant: C.R. BARD, INC., Murray Hill, NJ (US)

(72) Inventor: Hiep Do, Chandler, AZ (US)

(73) Assignee: C. R. BARD, INC., Murray Hill, NJ (US)

(*) Notice: Subject to any disclaimer, the term of this patent is extended or adjusted under 35 U.S.C. 154(b) by 773 days.

(21) Appl. No.: 16/323,925

(22) PCT Filed: Sep. 8, 2017

(86) PCT No.: PCT/US2017/045958
§ 371 (c)(1),
(2) Date: Feb. 7, 2019

(87) PCT Pub. No.: WO2018/031580
PCT Pub. Date: Feb. 15, 2018

(65) Prior Publication Data
US 2019/0209825 A1 Jul. 11, 2019

Related U.S. Application Data

(60) Provisional application No. 62/372,109, filed on Aug. 8, 2016.

(51) Int. Cl.
*A61M 39/02* (2006.01)
*A61M 25/10* (2013.01)
(Continued)

(52) U.S. Cl.
CPC .......... *A61M 39/0247* (2013.01); *A61M 1/14* (2013.01); *A61M 1/3655* (2013.01);
(Continued)

(58) Field of Classification Search
CPC .. A61M 39/0247; A61M 1/14; A61M 1/3655; A61M 25/1011; A61M 25/104;
(Continued)

(56) References Cited

U.S. PATENT DOCUMENTS 5,575,815 A 11/1996 Slepian et al.
5,894,011 A * 4/1999 Prosl ............... F16K 11/074
422/44

(Continued)

FOREIGN PATENT DOCUMENTS

CA 2536168 5/2005
CN 205268803 6/2016
(Continued)

OTHER PUBLICATIONS

Park et al., Balloon-assisted maturation for arteriovenous fistula maturation failure: an early period experience, Annals of Surgical Treatment and Research, May 2, 2016, 90(5): 272-278, the Korean Surgical Society.

(Continued)

*Primary Examiner* — Leslie R Deak
(74) *Attorney, Agent, or Firm* — Garvey, Smith & Nehrbass, Patent Attorneys, L.L.C.; Charles C. Garvey, Jr.; Fabian M. Nehrbass

(57) ABSTRACT

A method and apparatus are aimed to improve arteriovenous fistula maturation rate by treating the fistula with a crosslink agent solution (fixative solution). The fixative solution will crosslink proteins and biomolecules, allowing formation of crosslinks that stabilize or stable tissue structure. The method and apparatus will address factors that contribute to arteriovenous fistula maturation failure by stopping the neointimal hyperplasia growth after vascular injury and stabilizing the venous wall to prevent the lumen from narrowing.

9 Claims, 4 Drawing Sheets

(51) Int. Cl.
    *A61M 1/36*     (2006.01)
    *A61M 1/14*     (2006.01)
    *A61L 31/00*     (2006.01)
    *A61B 17/12*     (2006.01)

(52) U.S. Cl.
    CPC ...... *A61M 25/104* (2013.01); *A61M 25/1011* (2013.01); *A61B 17/12045* (2013.01); *A61B 17/12109* (2013.01); *A61B 17/12136* (2013.01); *A61L 31/00* (2013.01); *A61M 2025/1052* (2013.01); *A61M 2039/0258* (2013.01); *A61M 2039/0261* (2013.01); *A61M 2039/0276* (2013.01); *A61M 2039/0291* (2013.01); *A61M 2039/0297* (2013.01)

(58) Field of Classification Search
    CPC .. A61M 2039/0258; A61M 2039/0276; A61M 2039/0291
    See application file for complete search history.

(56) References Cited

U.S. PATENT DOCUMENTS

| | | |
|---|---|---|
| 6,808,518 B2 | 10/2004 | Wellman et al. |
| 8,486,155 B2 | 7/2013 | McAlister et al. |
| 8,911,468 B2 | 12/2014 | Ogle et al. |
| 2004/0059290 A1 | 3/2004 | Palasis |
| 2011/0218517 A1* | 9/2011 | Ogle ............... A61K 9/006 514/8.1 |
| 2015/0032087 A1 | 1/2015 | Haisha |
| 2015/0134049 A1 | 5/2015 | Austen, Jr. et al. |
| 2015/0209558 A1 | 7/2015 | Charlebois et al. |
| 2015/0320981 A1 | 11/2015 | Curtis |

FOREIGN PATENT DOCUMENTS

| | | |
|---|---|---|
| CN | 105749407 | 7/2016 |
| JP | 2007307429 | 11/2007 |
| WO | 9509659 | 4/1995 |
| WO | 2014070136 | 5/2014 |
| WO | 2016064076 | 4/2016 |

OTHER PUBLICATIONS

International Search Report, completed Oct. 30, 2017, dated Nov. 21, 2017.
Written Opinion of the International Searching Authority, completed Oct. 30, 2017, dated Nov. 21, 2017.
Extended European Search Report, dated Feb. 12, 2020 (8 pages).

* cited by examiner

METHOD AND APPARATUS FOR ENHANCING THE MATURATION RATE OF AN ARTERIOVENOUS FISTULA

CROSS-REFERENCE TO RELATED APPLICATIONS

This application claims the benefit of U.S. Provisional Patent Application Ser. No. 62/372,109, filed 8 Aug. 2016. Priority of U.S. Provisional Patent Application Ser. No. 62/372,109, filed 8 Aug. 2016, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method and apparatus for enhancing or improving the arteriovenous fistula (AVF) maturation rate by treating the fistula with a crosslink agent solution (fixative solution) that will crosslink proteins and biomolecules thus enabling formation of crosslinks that stabilize the tissue structure.

2. General Background of the Invention

Arteriovenous fistulae are the preferred mode of dialysis vascular access due to low long-term rates of infection and stenosis. Patients with a functioning arteriovenous fistula or AVF live longer and cost less to treat as compared to patients dialyzing through a tunneled dialysis catheter (or TDC). Despite the many advantages of the native arteriovenous fistula, a number of studies have documented major problems with arteriovenous fistula maturation (failure to increase blood flow and diameter adequately to support dialysis) as a result of peri-anastomotic venous segment stenosis.

Recently a number of physicians have championed a more aggressive approach to arteriovenous fistula maturation failure in which repeated long segment angioplasty procedures are used to sequentially dilate up the perianastomotic venous segment. Even though there are some successes with these procedures, there are also negative consequences with respect to pathology and pathogenesis of arteriovenous fistula maturation failure. At a biology level, an aggressive neointimal hyperplasia growth is most likely to migrate from the media or adventitia. At a pathogenetic level, it is likely that vascular injury is the initiator of neointimal hyperplasia and a lack of outward remodeling. Neointimal hyperplasia can be defined as an increase in the thickness of the lining of a blood vessel in response to injury or vascular reconstruction. It is an important cause of vein graft obstruction after coronary artery bypass surgery and in the premature closure of other vascular conduits, e.g., in dialysis access devices. It is characterized by the migration of smooth muscle cells into the graft, followed by the release of cytokines that damage the vessel wall and contribute to its degradation by inflammation.

Some patents have issued that relate generally to balloon treatment methods. The following possibly relevant U.S. Patent documents are incorporated herein by reference:

| Patent Document No. | TITLE |
| --- | --- |
| 8,911,468 | Devices, Therapeutic Compositions and Corresponding Percutaneous Treatment Methods for Aortic Dissection |
| 2015/0209558 | Articulating Balloon Catheter and Method for Using the Same |

BRIEF SUMMARY OF THE INVENTION

The present invention solves the problems confronted in the art in a simple and straightforward manner. The present invention provides a method and apparatus that is aimed to improve arteriovenous fistula (AVF) maturation rate by treating the fistula with a crosslink agent solution (fixative solution). The fixative solution will crosslink proteins and biomolecules, through the amine and/or carboxyl groups of collagen, allowing formation of crosslinks that stabilize tissue structure. The method and apparatus of the present invention will address factors that contribute to arteriovenous fistula maturation failure: (1) stop the neointimal hyperplasia growth after vascular injury and (2) stabilize the venous wall to prevent the lumen from narrowing.

The present invention is aimed to develop a therapy treatment that uses a specially configured double seal (e.g., dual balloon, such as inflatable balloons) catheter delivery system and a crosslink agent or fixative solution, to improve arteriovenous fistula maturation rate. The catheter delivery system provides a shaft and dual (spaced apart) seals or balloons at the distal end portion of the catheter. The seals or balloons are located or spaced apart a distance which equals to the targeted treatment length (e.g., between about 10 and 300 mm.). With the distance between the seal or balloon locations, there are infusers or ports or holes that allow for infusion and aspiration of a fixative solution. Prior to the insertion of the catheter of the present invention, the veins are enlarged to a predetermined size using angioplasty. For example, this predetermined size is approximately 6 mm diameter. Following the angioplasty, the veins are stabilized further by infusing of fixative solution. The fixative solution can be for example the following: oxidizing agents, glutaraldehyde, neutral buffered formalin, paraformaldehyde, dimethyl suberimidate, dimethyl 3,3-dithiobispropionimidate, aceyl azie, lysyl oxidase and transglutaminase. For example, it could be DMS (dimethyl suberimidate dihydrochloride) Product number 20700, by Thermo Scientific. The fixative solution will react with various proteins, including any collagen that contains amine groups and/or carboxyl groups, allowing formation of crosslinks that stabilize the vein segment tissue structure. As a consequence, most of the vascular injury response from balloon angioplasty is discouraged. The vein segment vessel wall will become hardened due to the cross-linking of proteins.

The treatment can be applied either prior or post arteriovenous fistula creation. Initially, the vein segment can be subjected to multiple angioplasties for enlargement of the vessel lumen. The dual balloon catheter is then percutaneously delivered to the intended vein segment and inflated to block off blood flows in both directions. The residual blood within the lumen is aspirated and washed with saline to ensure that it is free of blood. The fixative solution is then infused into the vein lumen and incubated for a predetermined time to allow for cross-linking of proteins. The fixative solution is removed when the incubation time is expired. The incubation time is preferably dependent on the concentration of the cross-linking agent and the desired degree of the cross-linking within the vessel wall. Preferably this time ranges from about 5 minutes up to about 12 hours. The incubation time is typically shorter when the concentration of the fixative solution used is higher, and the incubation time is longer when the desired degree of cross-linking within the vessel wall is greater. One of ordinary skill in the art can determine the desired incubation time without undue experimentation.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
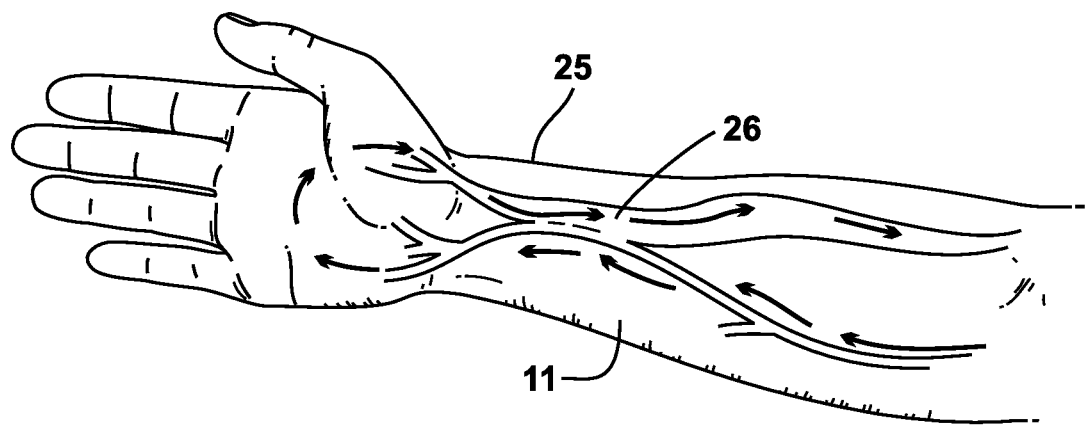
FIGS. 1 and 2 are schematic diagrams showing the method of the present invention and the preferred embodiment of the apparatus of the present invention.
Figure 2:
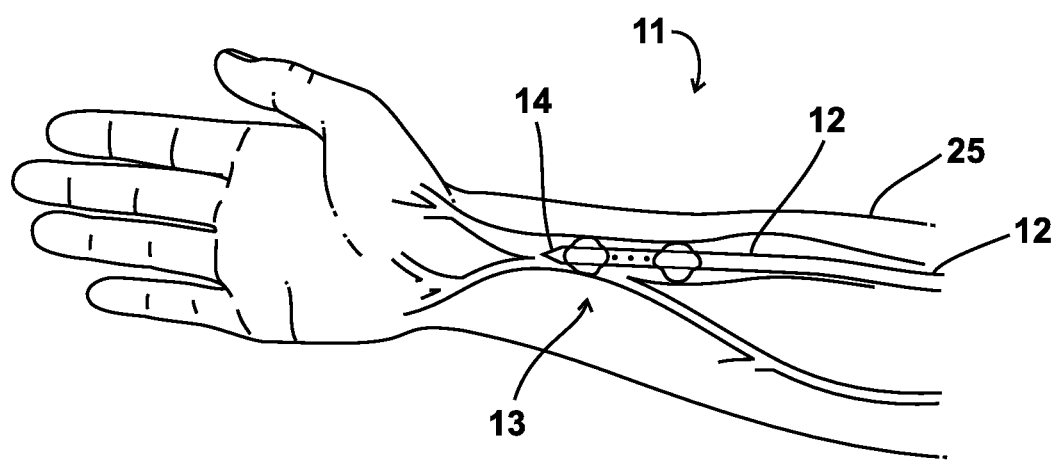
Figure 6:
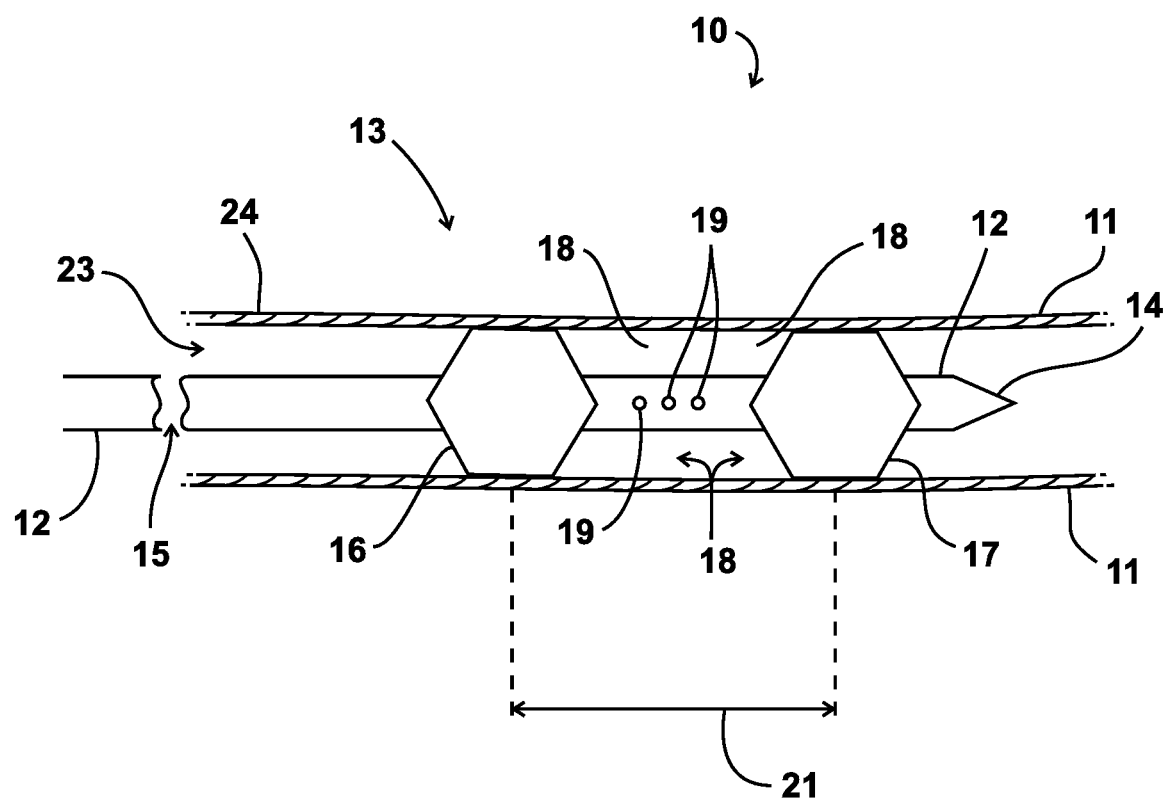
FIGS. 6-7 are schematic diagrams of preferred embodiments of the apparatus of the present invention.
Figure 7:
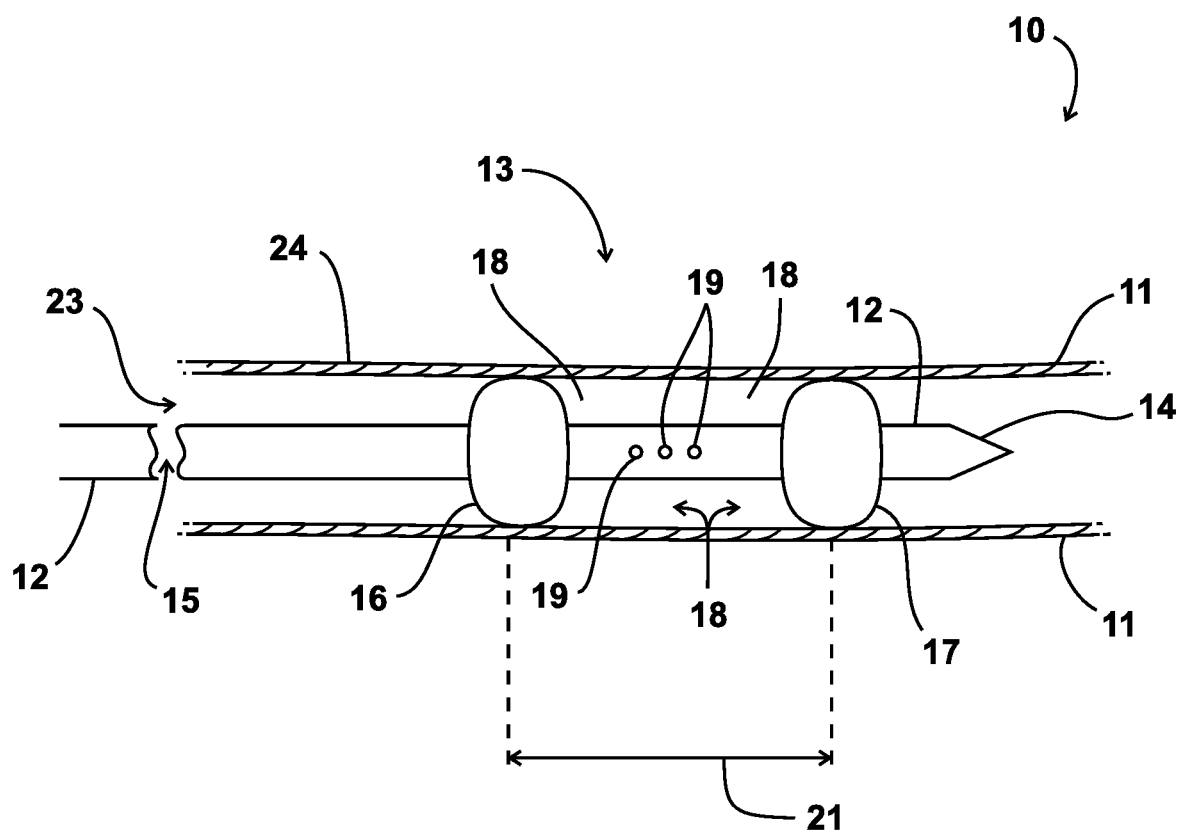

FIGS. 1 and 2 are schematic diagrams showing a patient's arm 25 and an arteriovenous fistula 26, arteriovenous fistula maturation rate improvement apparatus 10 is placed in a targeted vein segment 11. The segment or vein 11 has a vein lumen 23 surrounded by a vein or vessel wall 24. A catheter 12 is configured to be inserted into vein segment 11 lumen 23 as shown in FIGS. 1 and 2. Catheter 12 has distal end portion 13 with tapered tip 14. Catheter 12 has lumen or bore 15 and ports or openings 19 that together with catheter bore 15 enable infusion of fluid to the vein segment 11 (see FIG. 6).

A pair of seals, seal members or inflatable balloons 16, 17 are mounted on catheter 12. Seals 16, 17 are spaced apart a distance 21 (e.g., between about 10 and 300 mm). Catheter 12 has infusers, ports or openings 19 that enable transmission of a desired fixation solution 20 into the space 18 between seals 16, 17 and between catheter 12 and vessel wall 24. Alternatively, surgical clips could be used at the time of fistula creation to create the seal at either end.

Figure 3:
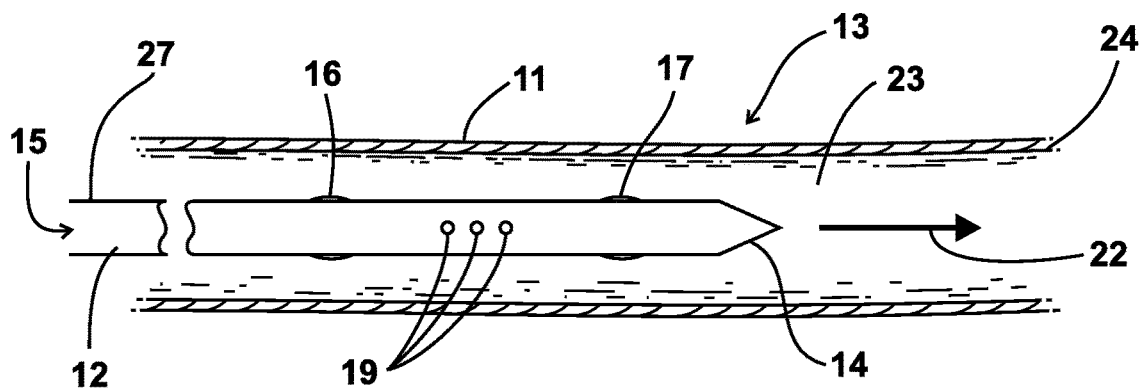
FIGS. 3-5 are sequential views that illustrate the method and apparatus of the present invention.
Figure 4:
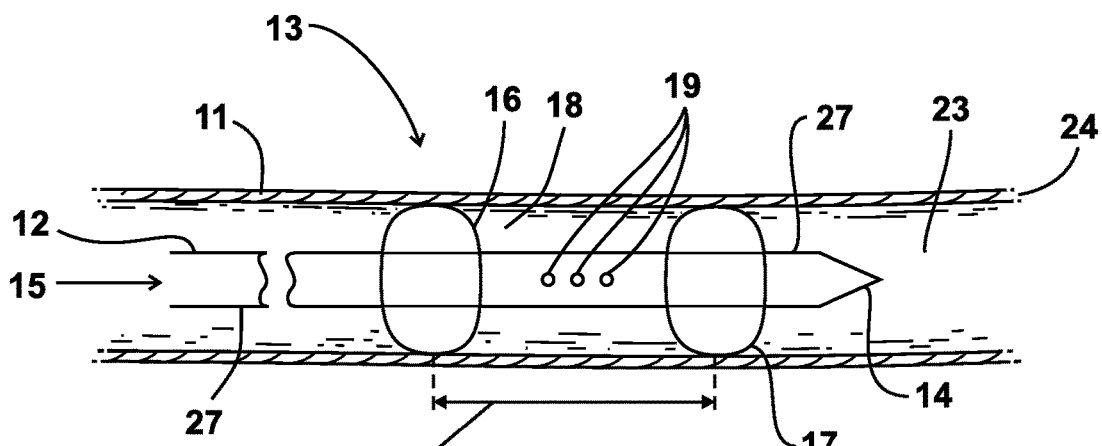
Figure 5:
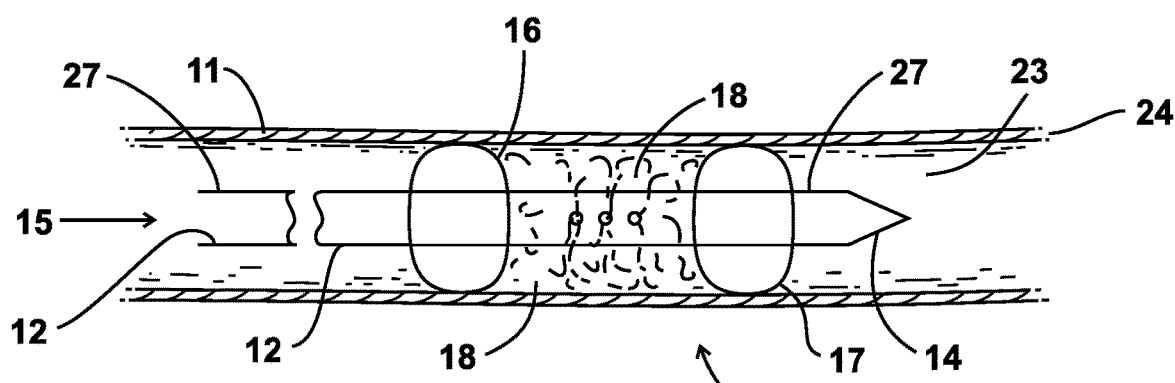

FIGS. 3-5 show the method of the present invention. In FIG. 3, a catheter 12 having spaced apart seals 16, 17 (e.g., inflatable or inflation balloons), distal end portion 13, tip 14 and catheter lumen 15 is inserted into a patient's vascular system as indicated by arrow 22 and placed next to or at the targeted vein segment 11.

In FIG. 4, each seal 16, 17 is expanded radially wall 27 and circumferentially from catheter 12 to engage and seal against the vessel segment 11 wall 24. A space 18 is thus isolated between seals 16, 17 and between catheter 12 wall 27 and vein segment 11 wall 24. It is this space 18 that is filled with a selected fixation solution 20 as seen in FIG. 5. The fixation solution 20 remains in space 18 for a selected incubation time sufficient to enable or allow cross linking of collagen (between about 5 minutes and 12 hours). Fixation solution 20 can be a commercially available solution, such as from Thermo Scientific company and sold under the designation DMS (dimethyl suberimidate dihydrochloride).

The present invention will address two important factors that contribute to AVF maturation failure: (1) stop the neointimal hyperplasia growth after vascular injury and (2) stabilize the venous wall to prevent the lumen from narrowing.

This invention preferably includes a therapy treatment system, the treatment system comprises: (a) a dual balloon catheter delivery system 10, and (b) a crosslink agent solution 20, to improve AVF maturation rate. The catheter delivery system 10 preferably comprises a shaft 12 with two balloons 16, 17 at the distal end 13. The balloons 16, 17 are preferably spaced between 10 and 100 mm apart, which equals the targeted treatment length. Within the distance between the balloon locations, there are preferably infusers or holes 19 that allow for infusion and aspiration of the fixative solution 20. The fixative solution 20 can be one or more of the following: oxidizing agents, glutaraldehyde, neutral buffered formalin, paraformaldehyde, dimethyl suberimidate, dimethyl 3,3-dithiobispropionimidate, aceyl azie, lysyl oxidase and transglutaminase. For example, the fixative solution 20 could be DMS (dimethyl suberimidate dihydrochloride) Product number 20700, by Thermo Scientific. The fixative solution 20 will preferably react with various proteins, including any collagen that contains amine groups and/or carboxyl groups, allowing formation of cross-links that stabilize the vein segment 11 tissue structure. The fixative solution 20 will preferably react with various proteins and other biomolecules, allowing formation of cross-links that stabilize the tissue structure. As a consequence, most of the vascular injury response that may be caused by balloon angioplasty is discouraged. Additionally, the vessel wall 24 will harden due to the cross-linking of proteins.

The treatment system of the present invention can be applied either prior to or post AVF creation. Preferably, the vein segment 11 is first subjected to multiple angioplasties for enlargement of the lumen 23 to a determined size (for example, 6 mm diameter). Next, the dual balloon catheter 10 of the present invention is preferably percutaneously delivered to the intended vein segment 11 and preferably inflated to block off blood flow in both directions. Preferably, the residual blood within the lumen is aspirated and washed with saline to ensure the treatment area is free of blood. Then the fixative solution 20 is preferably infused into the vein lumen 23 and incubated for a predetermined time to allow for cross-linking of proteins. The fixative solution 20 is preferably removed when the incubation time is expired. The predetermined time can be between 5 minutes and 12 hours, for example. One with ordinary skill in the art will be able to determine the proper incubation time based on the concentration of fixative solution and the level of stability desired of the vessel.

The present invention includes a method of improving arteriovenous fistula 26 maturation rate using the system of the present invention 10. The method comprises the steps of:

a) identifying an arteriovenous fistula vein segment 11 to be treated, said segment 11 having a vein segment wall 24 and a vein segment lumen 23;

b) placing a catheter 12 in the vein segment lumen 23, the catheter 12 having a catheter wall 27, an outer surface, an inner surface, a catheter bore 15, and one or more openings 19 in said wall 27;

c) wherein in step "b" the catheter 12 has spaced apart first 16 and second seals 17, each seal 16, 17 enabling a seal to be made between the vein segment wall 24 and the catheter outer surface;

d) transmitting a volume of a fixative solution 20 via the catheter bore 15 and catheter opening or openings 19 into a space that is in between the seals 16, 17 of step "c" and in between the catheter 12 and vein segment wall 24; and e) retaining the fixative solution 20 in said space for an incubation time period sufficient to allow cross linking of proteins.

The incubation time of step "e" is preferably between about 5 minutes and 12 hours. More preferably, the incubation time of step "e" is at least 5 minutes.

Preferably, the incubation time of step "e" is dependent on the concentration of the fixative solution 20 used in step "d" and the desired degree of crosslinking within the vessel wall 24.

In a preferred embodiment, at least one of the seals 16, 17 of step "c" is an inflatable seal. More preferably, at least one of the seals 16, 17 of step "c" is an inflatable balloon.

Preferably, both seals 16, 17 are inflatable balloons.

Preferably, the spacing the seals 16, 17 apart is between about 10 and 300 mm. Preferably, the catheter 12 of step "b" has a bore 15 with a bore diameter of between about 0.1 and 2 mm.

In a preferred embodiment, the method further includes a preliminary step of subjecting the vein segment 11 to at least one angioplasty. More preferably, this preliminary step involves subjecting the vein segment 11 to multiple balloon angioplasties.

Preferably, the volume of fixative solution 20 in step "d" is between about 1 and 25 milliliters.

The present invention includes an arteriovenous fistula vein segment maturation rate improvement apparatus. The apparatus comprises (a) a catheter 12 having proximal and distal 13 portions, a catheter wall 27, a catheter bore 15, and one or more flow ports 19 through said catheter wall 27; (b) first and second seals 16, 17 mounted to the catheter 12 at spaced apart 21 positions; (c) the catheter 12 and seals 16, 17 being configured to be positioned within the lumen 23 of a vein segment 11 to be treated; (d) the seals 16, 17 being movable between a first position that enables insertion into the vein segment lumen and a second position that forms a seal between the catheter wall 27 and the vein segment 11; (e) a volume of a fixation solution 20 that occupies a space 18 that is in between the seals 16, 17 when in the second position and in between the catheter 12 and the vein segment wall 24; (0 wherein the fixative solution 20 promotes cross linking of proteins of the vein segment 11; and (g) wherein one or both of the seals 16, 17 has a first diameter when in said first position and a second diameter that is longer than said first diameter when in said second position.

Preferably, at least one of said seals 16, 17 is an inflatable seal. More preferably, both of said seals 16, 17 is an inflatable seal. More preferably, each of the seals 16, 17 is an inflatable balloon. Most preferably, each of the seals 16, 17 is an inflatable balloon.

Preferably, the seals 16, 17 are spaced apart 21 between about 10 and 300 mm.

Preferably, the volume of fixation solution 20 is between about 1 and 25 milliliters (ml).

Preferably, the catheter 12 has a diameter of between about 0.33 and 5 mm.

Preferably, the catheter bore 15 has a diameter of between about 0.1 and 1 mm.

The present invention includes an arteriovenous fistula maturation rate improvement apparatus, comprising: (a) a catheter 12 having proximal and distal 13 portions, a catheter wall 27, a catheter bore 15, and one or more flow ports 19 through said catheter wall 27; (b) first and second seals 16, 17 mounted to the catheter 12 at spaced apart positions a distance 21; (c) the catheter 12 and seals 16, 17 being configured to be positioned within the lumen 23 of a vein segment 11 to be treated; (d) the seals 16, 17 being movable between a first and collapsed position that enables insertion into the vein segment lumen 23 and a second and expanded position that forms a seal between the catheter wall 27 and the vein segment 11; (e) a volume of a fixation solution 20 that occupies a space 18 that is in between the seals 16, 17 when in the second position and in between the catheter 12 and the vein segment wall 24; (0 wherein the fixation solution 20 promotes cross linking of proteins of the vein segment 11; (g) wherein one or both of the seals 16, 17 has a first diameter when in said first position and a second diameter that is greater than said first diameter when in said second position; and (h) wherein in said second position the seals 16, 17 each have an extended diameter of between 2 and 10 mm and the catheter wall 27 between said seals 16, 17 has a diameter that is less than said extended diameter.

Preferably, the incubation time of step "e" is shorter when the concentration of the fixative solution 20 used in step "d" is higher, and the incubation time of step "e" is longer when the desired degree of crosslinking within the vessel wall 24 is greater.

The following is a list of parts and materials suitable for use in the present invention:

PARTS LIST:

| PART NUMBER | DESCRIPTION |
|---|---|
| 10 | arteriovenous fistula maturation rate enhancement system |
| 11 | vein segment/vein |
| 12 | catheter |
| 13 | distal end/distal end portion |
| 14 | tapered tip |
| 15 | catheter lumen/catheter bore |
| 16 | first seal member/first balloon |
| 17 | second seal member/second balloon |
| 18 | space |
| 19 | infusers/apertures/openings |
| 20 | fixation solution |
| 21 | distance/spacing |
| 22 | arrow |
| 23 | vein lumen |
| 24 | vein wall/vessel wall |
| 25 | arm |
| 26 | arteriovenous fistula |
| 27 | catheter wall |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method of improving arteriovenous fistula maturation rate by stopping neointimal hyperplasia growth and stabilizing a venous wall to prevent a vein segment lumen from narrowing, comprising the steps of:

a) identifying an arteriovenous fistula vein segment to be treated, said segment having a vein segment inner wall surface and a vein segment lumen;
b) subjecting the vein to one or more angioplasties to enlarge the vein to a predetermined size of at least 6 mm diameter;
c) placing a catheter in the vein segment lumen, the catheter having a catheter wall, an outer surface, an inner surface, a catheter bore, and one or more openings in said wall;
d) wherein in step "c" the catheter has spaced apart first and second seals, each seal enabling a seal to be made between the vein segment wall and the catheter outer surface;
e) aspirating and washing with saline any residual blood in a space that is in between the seals and in between the catheter and vein segment wall;
f) transmitting a volume of a fixative solution via the catheter bore and catheter opening or openings into the space;
g) retaining the fixative solution in said space for an incubation time period between about 5 minutes and 12 hours to allow cross linking of proteins of the vein segment wall;
h) removing the fixative solution after the incubation time period of step "g";
i) wherein during steps "g" and "h" the fixative solution contacts the fistula vein segment inner wall surface; and
j) wherein steps "a" through "i" stop neointimal hyperplasia growth and stabilize the venous wall to prevent the lumen from narrowing.

2. The method of claim 1 wherein at least one of the seals is an inflatable seal.

3. The method of claim 1 wherein at least one of the seals is an inflatable balloon.

4. The method of claim 1 further comprising the step of spacing the seals apart between about 10 and 300 mm.

5. The method of claim 1 wherein the catheter of step "c" has a bore with a bore diameter of between about 0.1 and 2 mm.

6. The method of claim 1 wherein in step "f" the volume of fixative solution is between about 1 and 25 milliliters.

7. The method of claim 1 wherein the incubation time of step "g" is dependent on the concentration of the fixative solution used in step "f" and the desired degree of crosslinking within the vessel wall.

8. The method of claim 7 wherein the incubation time of step "f" is shorter when the concentration of the fixative solution used in step "e" is higher, and the incubation time of step "f" is longer when the desired degree of crosslinking within the vessel wall is greater.

9. The method of claim 1 wherein the catheter has a distal end portion having a tapered tip.

* * * * *

UNITED STATES PATENT AND TRADEMARK OFFICE
CERTIFICATE OF CORRECTION

PATENT NO. : 11,464,959 B2  
APPLICATION NO. : 16/323925  
DATED : October 11, 2022  
INVENTOR(S) : Hiep Do Page 1 of 1

It is certified that error appears in the above-identified patent and that said Letters Patent is hereby corrected as shown below:

On the Title Page

Please correct, (22) to read as follows: "PCT Filed: Aug. 8, 2017"

Signed and Sealed this  
Twentieth Day of June, 2023

Katherine Kelly Vidal  
*Director of the United States Patent and Trademark Office*